(12) United States Patent
Peters

(10) Patent No.: US 11,660,712 B1
(45) Date of Patent: May 30, 2023

(54) METHOD OF ASSEMBLING A MEASUREMENT MODULE FOR A SURGICAL HANDPIECE SYSTEM

(71) Applicant: Stryker Corporation, Kalamazoo, MI (US)

(72) Inventor: Stephen Frederick Peters, Hickory Corners, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/733,064

(22) Filed: Apr. 29, 2022

(51) Int. Cl.
*B23P 15/00* (2006.01)
*A61B 90/00* (2016.01)
*B29C 65/08* (2006.01)
*B29L 31/00* (2006.01)

(52) U.S. Cl.
CPC .............. *B23P 15/00* (2013.01); *A61B 90/06* (2016.02); *A61B 2090/062* (2016.02); *B29C 65/08* (2013.01); *B29L 2031/7546* (2013.01)

(58) Field of Classification Search
CPC ... B23P 15/00; A61B 90/06; A61B 2090/062; B29L 2031/7546
See application file for complete search history.

(56) References Cited

U.S. PATENT DOCUMENTS

| | | | |
|---|---|---|---|
| 10,159,495 B1* | 12/2018 | Lambert | A61B 17/1615 |
| 11,317,927 B2 | 5/2022 | Carusillo et al. | |
| 2021/0052285 A1 | 2/2021 | Carusillo | |
| 2021/0228245 A1* | 7/2021 | Geist | A61B 17/8872 |
| 2021/0378684 A1 | 12/2021 | Lambert et al. | |
| 2022/0211391 A1 | 7/2022 | Carusillo et al. | |

FOREIGN PATENT DOCUMENTS

| | | |
|---|---|---|
| WO | 2019035096 A1 | 2/2019 |
| WO | 2021072373 A1 | 4/2021 |
| WO | 2022031770 A1 | 2/2022 |
| WO | 2021072373 A9 | 6/2022 |

\* cited by examiner

*Primary Examiner* — Jun S Yoo
(74) *Attorney, Agent, or Firm* — Howard & Howard Attorneys PLLC

(57) ABSTRACT

A method of assembling a measurement module used for bore depth determinations in tissue. The measurement module has a housing. A gear having a plurality of gear teeth is disposed within and rotatably coupled to the housing. The measurement module further includes a bushing and a depth extension member having a plurality of rack teeth extending along a depth extension axis. The depth extension member is disposed within a bore of the bushing and the housing. The rack teeth of the depth extension member are arranged to be engaged by the gear teeth of the gear. The depth extension member is urged toward the gear so that the rack teeth are in meshed engagement with the gear teeth. The bushing is fixed to the housing while the depth extension member is urged toward the gear.

16 Claims, 9 Drawing Sheets

METHOD OF ASSEMBLING A MEASUREMENT MODULE FOR A SURGICAL HANDPIECE SYSTEM

BACKGROUND

Conventional medical and surgical procedures routinely involve the use of surgical tools and instruments which allow surgeons to approach and manipulate surgical sites. By way of non-limiting example, rotary instruments such as handheld drills are commonly utilized in connection with orthopedic procedures to address various musculoskeletal conditions, such as trauma, sports injuries, degenerative diseases, joint reconstruction, and the like. In procedures where handheld drills or similar surgical instruments are employed, rotational torque selectively generated by an actuator (e.g., an electric motor) is used to rotate a releasably-attachable drill bit or other surgical attachments at different speeds.

A surgical handpiece assembly drills bores in the tissue against which the drill bit is applied. One type of surgical procedure in which it is necessary to drill a bore is a trauma procedure to repair a broken bone. In this type of procedure, an elongated rod, sometimes called a nail, is used to hold the fractured sections of the bone together. To hold the nail in place, one or more bores are driven into the bone. These bores are positioned to align with complementary holes formed in the nail. A screw is inserted in each aligned bore and nail hole. The screws hold the nail in the proper position relative to the bone.

In another type of procedure, an implant known as a plate is secured to the outer surfaces of the fractured sections of a bone to hold the sections together. Screws hold the plate to the separate sections of bone. To fit a screw that holds a plate to bone it is necessary to first drill a bore to receive the screw.

As part of a procedure used to drill a screw-receiving bore in a bone, it is desirable to know the end-to-end depth of the bore. This information allows the surgeon to select size of screw that is fitted in the bore hole. If the screw is too short, the screw may not securely hold the nail into which the screw is inserted in place. If the screw is too long, the screw can extend an excessive distance out beyond the bone. If the screw extends an excessive distance beyond the bone, the exposed end of the screw can rub against the surrounding tissue. If this event occurs, the tissue against which the screw rubs is affected.

While surgical drills are routinely utilized to assist in the performance of a variety of different types of medical and/or surgical procedures, there is a need in the art to continuously improve such surgical drills.

SUMMARY

The present disclosure provides method of assembling a measurement module used for bore depth determinations in tissue. The measurement module has a housing. The measurement module further includes a gear having a plurality of gear teeth disposed within and rotatably coupled to the housing. The measurement module also includes a bushing. The measurement module also includes a depth extension member extending along a depth extension axis and having a plurality of rack teeth. The method includes the step of disposing the depth extension member within a bore of the bushing and at least a portion of the housing. The method further includes the step of arranging the rack teeth of the depth extension member to be engaged by the gear teeth of the gear. The method further includes the step of urging the depth extension member toward the gear and the rack teeth into meshed engagement with the gear teeth. The method further includes the step of fixing the bushing to the housing while the depth extension member is urged toward the gear.

DETAILED DESCRIPTION

Figure 1:
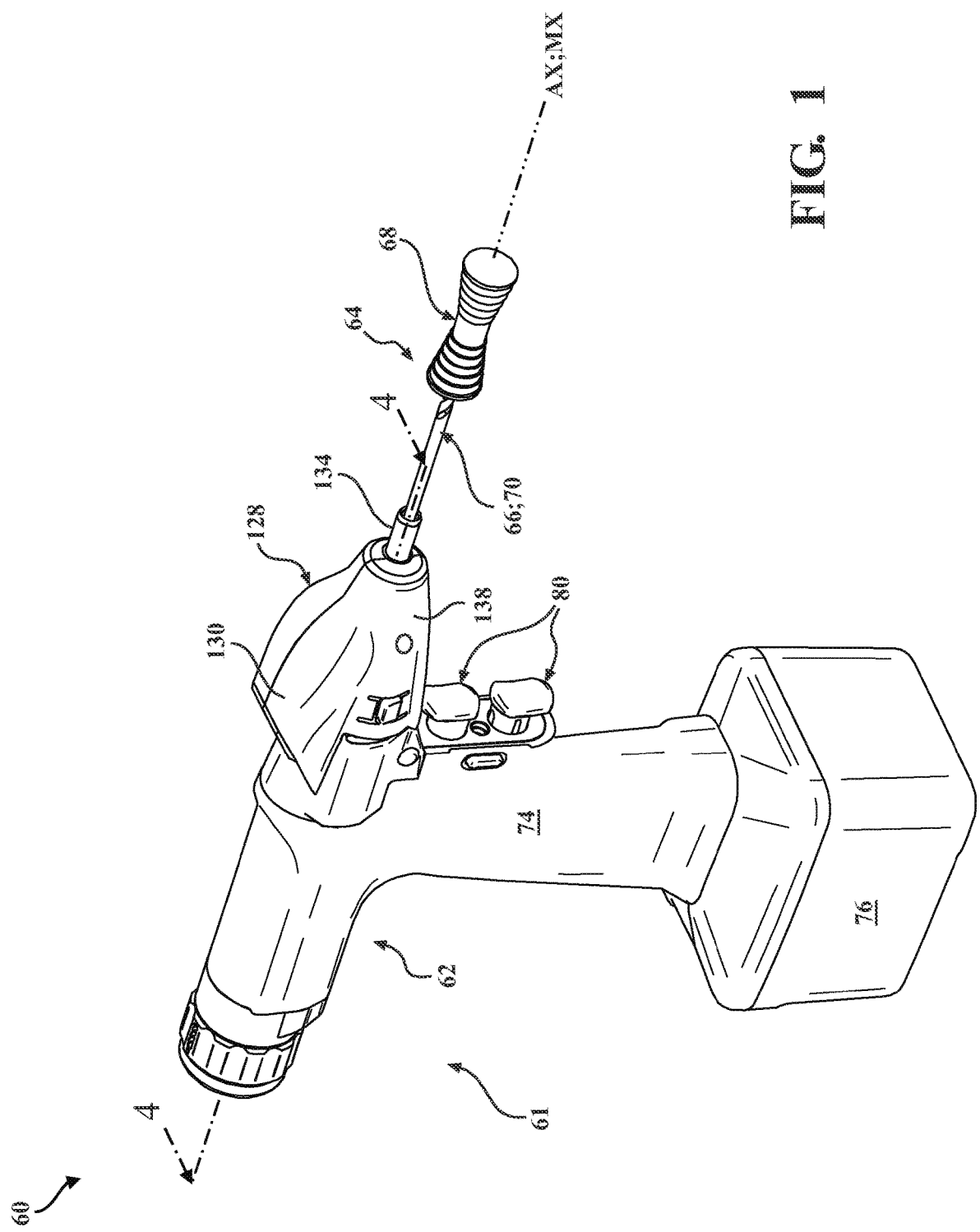
FIG. 1 is a perspective view of a surgical handpiece system comprising a surgical handpiece assembly and a measurement module, the surgical handpiece assembly shown having a drill bit according to one configuration.
Figure 2:
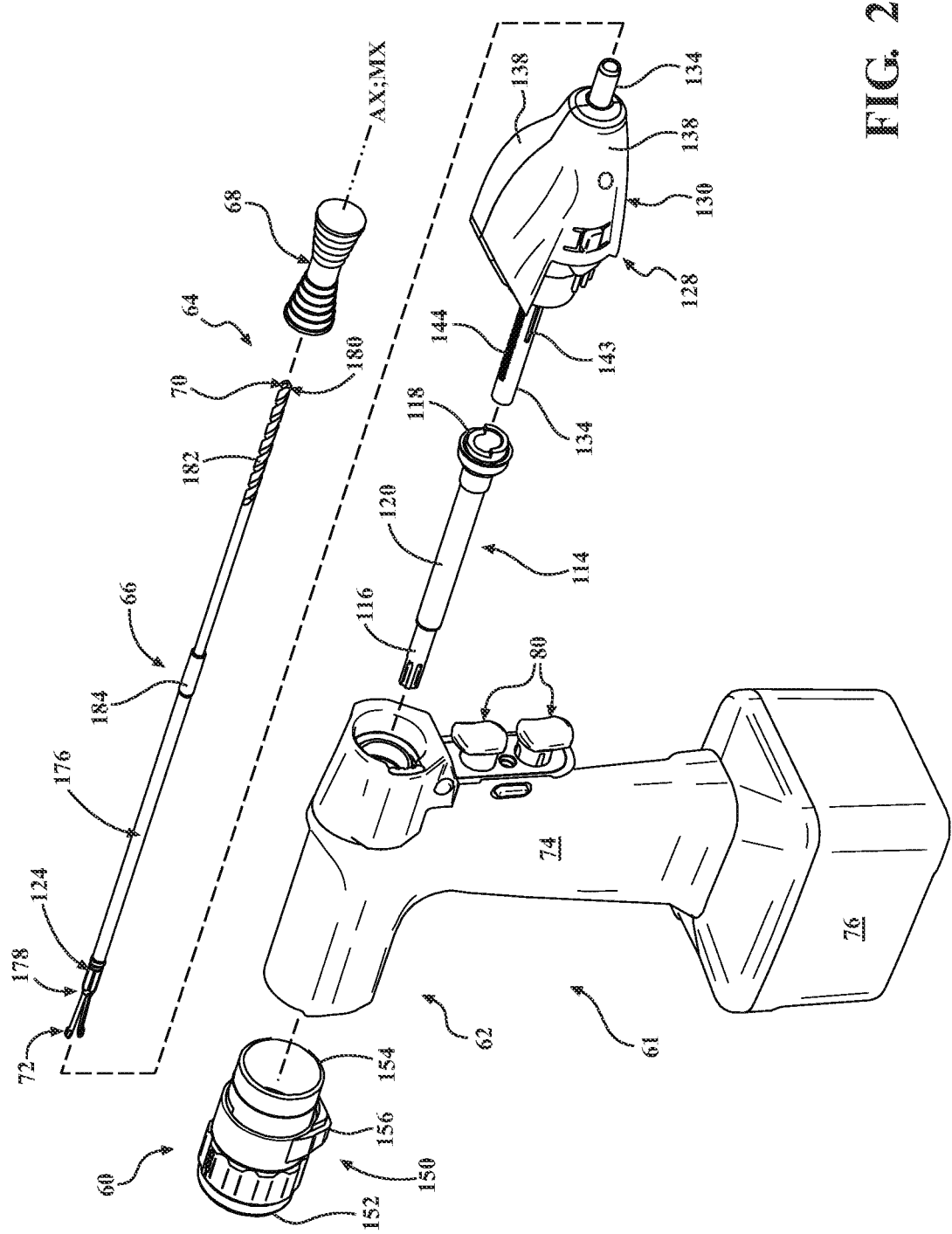
FIG. 2 is a partially-exploded perspective view of the surgical handpiece system of FIG. 1, with the surgical handpiece system shown having a measurement module, a drive cannula, and a release assembly spaced from a handpiece housing assembly, and with the end effector assembly removed from the surgical handpiece assembly.

With reference to the drawings, where like numerals are used to designate like structure throughout the several views, a surgical system, or surgical drill system, is shown at 60 in FIGS. 1-2 for performing an operational function associated with medical and/or surgical procedures. In some configurations, the surgical drill system 60 may also be referred to as a surgical handpiece system. In the representative configuration illustrated herein, the surgical handpiece system 60 is employed to facilitate penetrating a workpiece, such as tissue or a bone of a patient. To this end, the illustrated configuration of the surgical handpiece system 60 comprises a surgical drill 61 that comprises a handpiece 62, alternatively referred to as a handheld surgical instrument, and a drill bit 66. As is best depicted in FIG. 2, the drill bit 66 extends generally longitudinally along an axis AX between a cutting tip portion, generally indicated at 70, and an insertion portion, generally indicated at 72. As is described in greater detail below, the cutting portion 70, sometimes referred to as a cutting tip portion, is configured to engage tissue, and the insertion portion 72 is configured to facilitate releasable attachment of the drill bit 66 to the surgical handpiece assembly 62. Various configurations of the insertion portion 72 are contemplated to enable coupling of the drill bit 66 to the handpiece 62, such as various grooves, slots, and other geometries. One exemplary configuration of an insertion portion can be found in U.S. Pat. No. 10,159,495, which is hereby incorporated by reference in its entirety. It is contemplated that there may be other configurations to facilitate attachment of the drill bit 66 to the handpiece 62.

As also shown in FIG. 2, the drill bit 66 extends along the axis AX from a proximal end to a distal end. The cutting portion 70 may define flutes 182 which may be helically disposed about the axis AX and extend proximally from a distal end of the drill bit 66 to promote workpiece, such as tissue, penetration (see FIG. 2). The drill bit 66 comprises a shank portion, generally indicated at 176, which extends along the axis AX between the insertion portion 72 and the cutting portion 70. The shank portion 176 may vary in thickness along its length. In the configuration illustrated in FIG. 2, the shank portion 176 of the drill bit 66 may also include a bearing region 184 coupled to the shank portion 176. The bearing region 184 is sized so as to be received within and rotate relative to a depth extension member 134 of a measurement module 128 that may be coupled to the handpiece (discussed in greater detail further below). Here, the bearing region 184 may define a "stepped" outer region of the shank portion 176 that affords rotational support along the length of the drill bit 66, and may have a larger diameter than adjacent distal and proximal regions of the shank portion 176 in the illustrated configuration. However, it will be appreciated that the bearing region 184 of the shank portion 176 of the drill bit 66 could be configured in other ways without departing from the scope of the present disclosure.

Referring now to FIGS. 1-4, in the representative configuration illustrated herein, the handpiece 62 is realized as a handheld drill with a pistol-grip shaped handpiece body 74 which releasably attaches to a battery 76 (battery attachment not shown in detail). However, it is contemplated that the handpiece body 74 can have any suitable shape with or without a pistol grip. While the illustrated handpiece 62 employs a battery 76 which is releasably attachable to the handpiece body 74 to provide power to the handpiece 62 utilized to rotate the drill bit 66, it will be appreciated that the handpiece 62 may be configured in other ways, such as with an internal (e.g., non-removable) battery, or with a tethered connection to an external console, power supply, and the like. Other configurations are contemplated.

Figure 3:
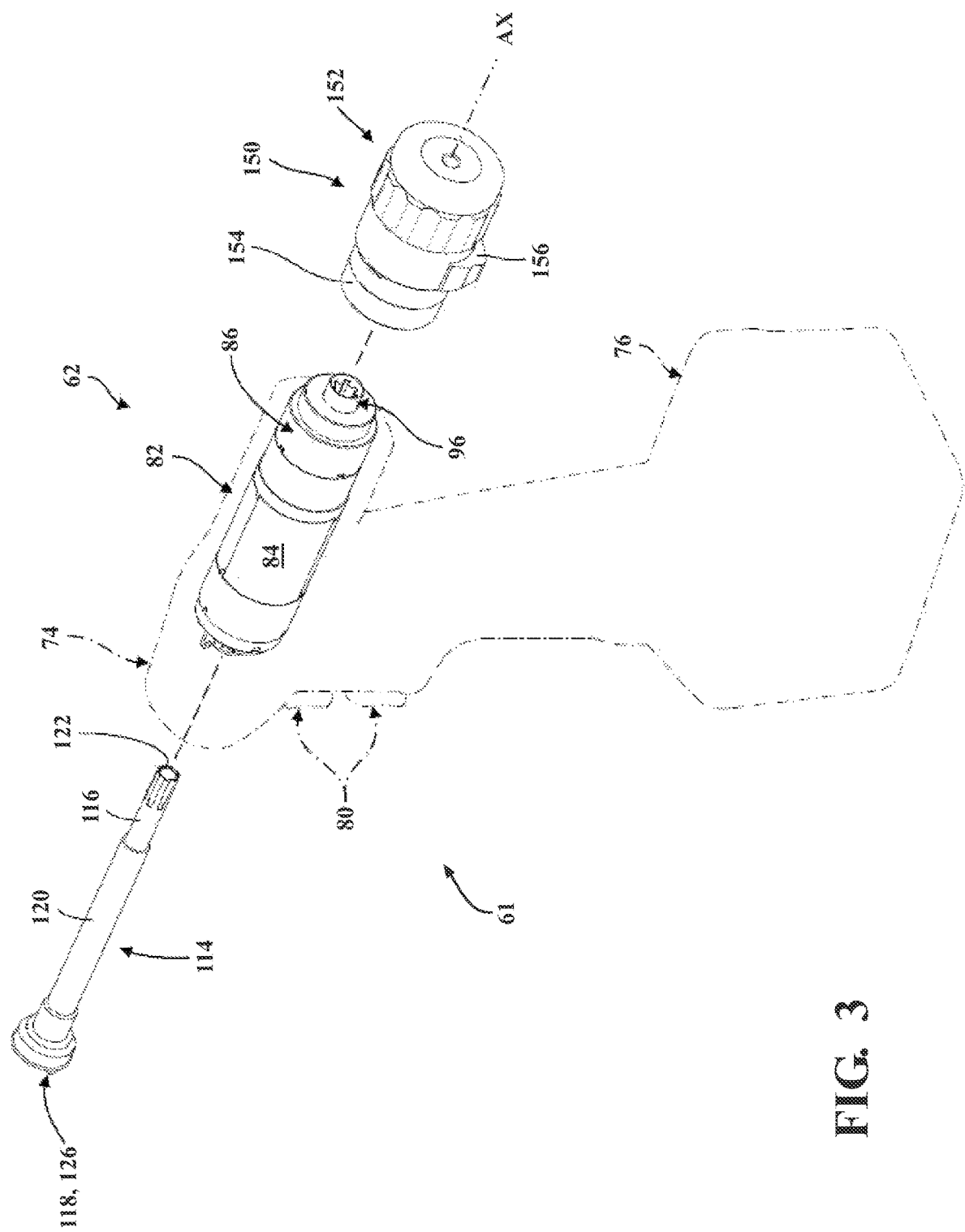
FIG. 3 is a partially-exploded perspective view of portions of the surgical instrument of FIGS. 1-2, shown with the drive assembly and the release mechanism spaced from a phantom outline of the handpiece body to depict an actuator assembly.

In the illustrated configuration, the battery 76 or other power source provides power to a controller 78, which is disposed in communication with an input control 80 and an actuator assembly 82 (see also FIG. 3). The input control 80 and the actuator assembly 82 are each supported by the handpiece body 74. The controller 78 is generally configured to facilitate operation of the actuator assembly 82 in response to actuation of the input control 80. The input control 80 has a trigger-style configuration in the illustrated configuration, is responsive to actuation by a user (e.g., a surgeon), and communicates with the controller 78, such as via electrical signals produced by magnets and Hall effect sensors. Thus, when the operator actuates the input control 80 to operate the handpiece 62, the controller 78 directs power from the battery 76 to the actuator assembly 82 which, in turn, generates rotational torque employed to rotate the drill bit 66, as described in greater detail below. The handpiece body 74, the battery 76, the controller 78, and the input control 80 could each be configured in a number of different ways to facilitate generating rotational torque without departing from the scope of the present disclosure.

Figure 5:
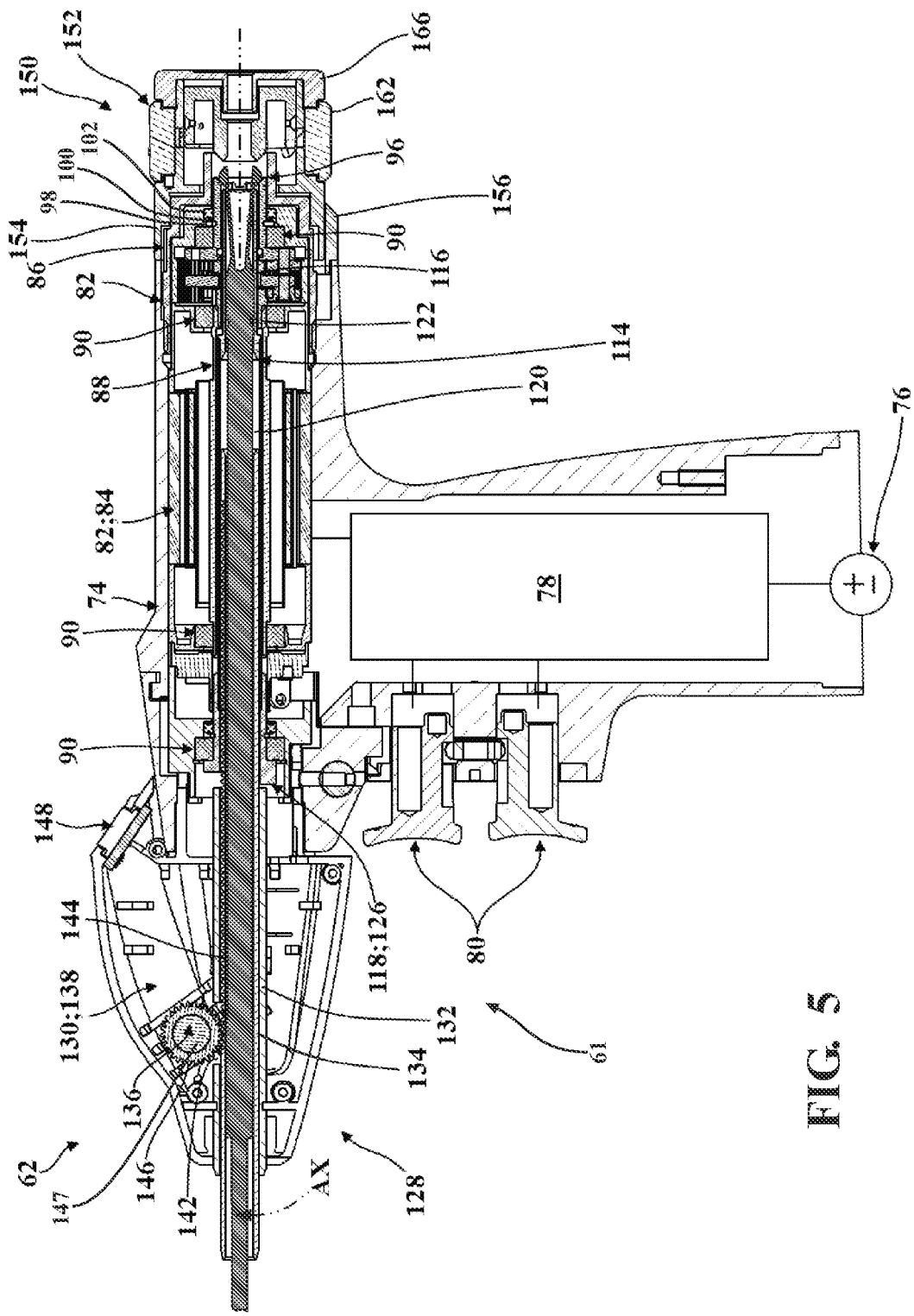
FIG. 5 is a sectional view taken longitudinally through the surgical instrument of FIGS. 1-4.

Referring As also shown in FIG. 3, the actuator assembly 82 may comprise an electric motor 84 and a gearset 86 which are each supported within the handpiece body 74. The motor 84 is configured to selectively generate rotational torque in response to commands, signals, and the like received from the controller 78. As is best shown in FIG. 5, the motor 84 comprises a rotor cannula 88 supported for rotation about the axis AX by a pair of bearings 90. A drive gear arranged adjacent to the gearset 86 is coupled to and rotates concurrently with the rotor cannula 88, and is employed to transmit rotational torque to the gearset 86. To this end, in the illustrated configuration, the gearset 86 is realized as two-stage compound planetary arrangement and generally comprises a ring gear housing 94 which, among other things, rotationally supports an output hub 96 via a bearing 90, as well as one or more retaining clips 98, washers 100, and/or seals 102. However, other configurations of the gearset 86 are contemplated.

Further details of one configuration of a gearset 86 are described, for example, in U.S. patent application Ser. No. 15/887,507, filed on Feb. 2, 2018 and entitled "Drill Bit for Handheld Surgical Instrument, the contents of which are herein incorporated by reference in their entirety, and describe wherein the rotation of the drive gear via actuation of the motor 84 effects concurrent rotation of the output hub 96, and wherein the output hub 96 rotates concurrently with the drill bit 66. The actuator assembly 82 could be configured in other ways without departing from the scope of the present disclosure. By way of non-limiting example, while the illustrated actuator assembly 82 employs a compound planetary arrangement to adjust rotational speed and torque between the drive gear of the motor 84 and the output hub 96, other types of gearsets 86 could be utilized in some configurations. Moreover, while the illustrated actuator assembly 82 employs an electrically-powered brushless DC motor to generate rotational torque, other types of prime movers could be utilized. Other configurations are contemplated.

As noted above, rotational torque generated by the motor 84 effects rotation of the output hub 96 which, in turn, rotates concurrently with the coupled drill bit 66. To this end, and as is best shown in FIGS. 2-5, the handpiece 62 further comprises a drive assembly 114 which generally extends through the various cannulated components of the actuator assembly 82 into splined engagement with the output hub 96 of the gearset 86. The drive assembly 114 is configured to facilitate releasable attachment between the drill bit 66 and the handpiece 62. The drive assembly 114 generally comprises a drive element 116 such as a drive cannula, a driving head 118, and a driving body 120 which extends between, and rotates concurrently with, the drive element 116 and the driving head 118. The drive assembly 114 is supported for rotation about the axis AX within the handpiece body 74 via splined engagement with the output hub 96 adjacent the drive element 116, and via an arrangement of bearings, washers, and seals adjacent the driving head 118. It is contemplated that the drill bit 66 may be configured to attach to the handpiece 62 to receive torque in a manner different from that described above.

Further details of the drive assembly 114 are also described, for example, in U.S. patent application Ser. No. 15/887,507, the contents of which are also herein incorporated by reference in their entirety. In the illustrated configuration, the driving head 118 of the drive assembly 114 comprises a coupling, generally indicated at 126, which is provided to facilitate transmitting rotational torque when the handpiece 62 is utilized in connection with other applications besides rotating the drill bit 66 of the present disclosure. More specifically, the illustrated drive assembly 114 is configured such that the handpiece 62 can rotate, drive, or otherwise actuate a number of different types of surgical instruments, tools, modules, end effectors, and the like, which can be configured to engage and rotate concurrently with either the bore 122 of the drive element 116, or the coupling 126 of the driving head 118. It will be appreciated that this configuration allows the same handpiece 62 to be utilized in a broad number of medical and/or surgical procedures. However, it is contemplated that the drive assembly 114 could be configured differently in some configurations, such as to omit a driving head 118 with a coupling 126 in configurations where the handpiece 62 configured for dedicated use with the drill bit 66 of the present disclosure.

Referring back to FIGS. 1-3, the illustrated configuration of the handpiece 62 further comprises a release mechanism, or coupling mechanism, generally indicated at 150, configured to facilitate removal of the drill bit 66. The coupling mechanism 150 generally comprises a release subassembly 152, a keeper body 154, and a housing adapter 156. The keeper body 154 and the housing adapter 156 are respectively configured to secure the release subassembly 152 to the actuator assembly 82 and the handpiece body 74, and could be realized with a number of different configurations or could be integrated into other parts of the handpiece 62 in some configurations.

As noted above, the drill bit 66 generally extends along the axis AX between the cutting tip portion 70 and the insertion portion 72, and is configured for releasable attachment to the handpiece 62 described herein and illustrated throughout the drawings via engagement between the interface 124 of the drill bit 66 and the bore 122 of the drive element 116 of the drive assembly 114. The drive element 116, in turn, cooperates with the output hub 96 of the gearset 86 of the actuator assembly 82 to facilitate rotating the drill bit 66 about the axis AX.

Figure 4:
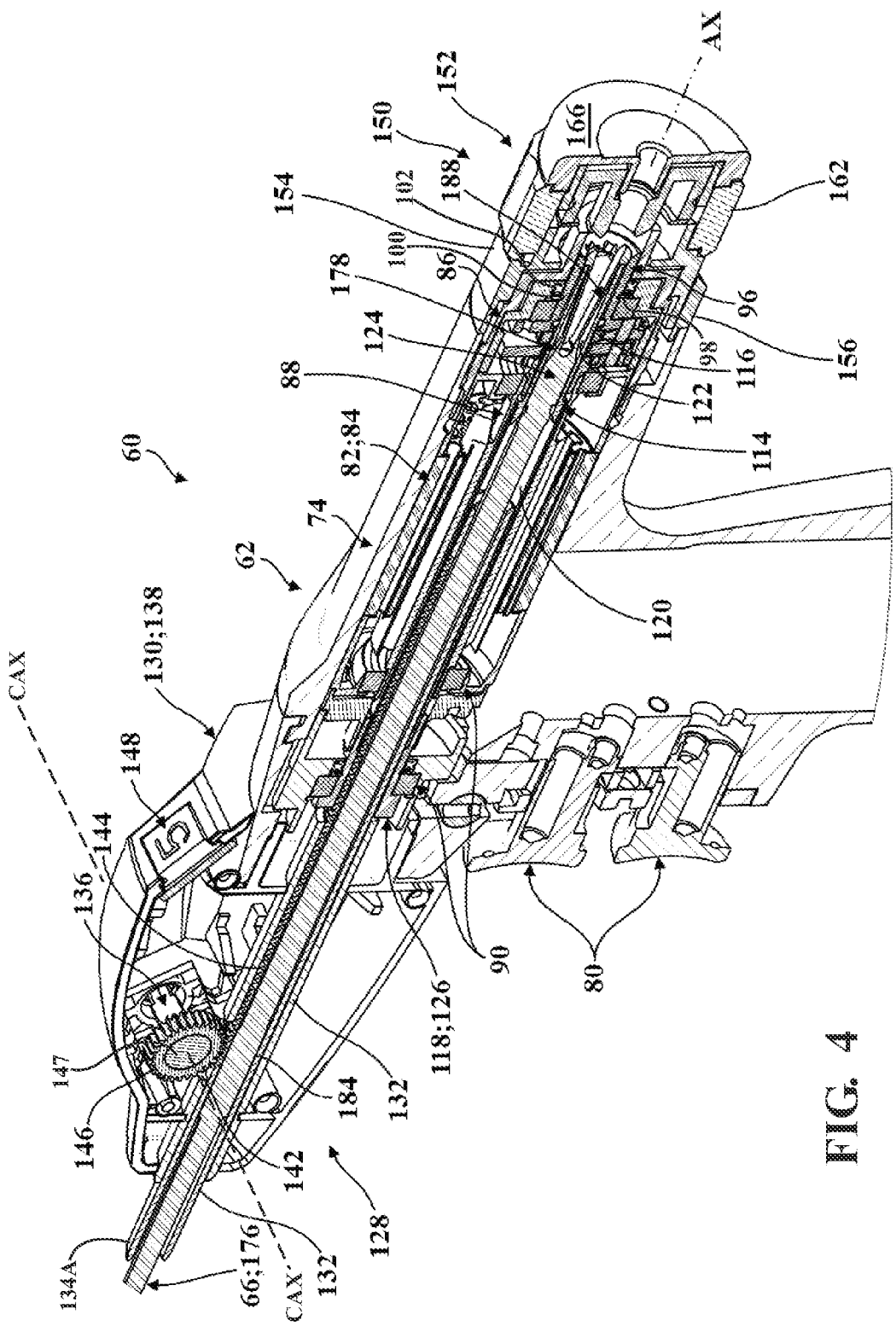
FIG. 4 is a partial isometric sectional view taken along line 4-4 in FIG. 1.

The illustrated configuration of the surgical drill system 60 further comprises the measurement module (alternatively referred to sometimes as a measurement head), generally indicated at 128, which may be configured to releasably attach to the handpiece 62 to provide the surgeon with measurement functionality during use. To this end, and as is best shown in FIGS. 4 and 5, the measurement module 128 may generally comprise a housing 130, a guide bushing 132, and a depth extension member 134 (i.e., a measurement probe, a depth measurement cannula, or a measurement cannula), which includes a distal end adapted for placement against a workpiece, or tissue. Suitable examples of a measurement module are described in International Patent Publication No. WO 2019/035096 A1, which is hereby incorporated by reference in its entirety. The housing 130 may be releasably attachable to the handpiece 62 and generally support the various components of the measurement module 128. The illustrated housing 130 may be formed as a pair of housing components 138 which interlock or otherwise attach together, and may be configured for disassembly to facilitate cleaning or servicing the measurement module 128. It should be appreciated that the measurement module 128 may be formed as an integral component of the handpiece 62, or may be in the form of a component that is affixed or otherwise secured to the handpiece 62 in a manner wherein the measurement module 128 is not removable from the handpiece 62 after use.

In the illustrated configuration, the housing components 138 and the guide bushing 132 comprise correspondingly-shaped features arranged to prevent relative axial and rotational movement therebetween, such as via notches formed in the guide bushing 132 which fit into webs or ribs formed in the housing components (not shown in detail). The guide bushing 132 may further comprise a window 142 as described in detail below. The guide bushing 132 may be fixed to the housing 130. Specifically, the guide bushing 132 may be fixed to the housing 130 by ultra-sonic welding the bushing 132 to the housing 130. In other configurations, the bushing 132 may be fixed to the housing 130 by applying an adhesive or a solvent to at least one of the bushing 132 and the housing 130. In still other configurations, the bushing 132 may be fixed to the housing 130 otherwise.

The depth extension member 134 may be disposed within a bore of the guide bushing 132 and is supported for translational movement along a depth extension axis DX, which may be aligned with the axis AX of the handpiece 62 when the measurement module 128 is coupled to the handpiece 62. An elongated recessed slot 143 (partially depicted in FIG. 2) may be formed transversely into the depth extension member 134 and extends longitudinally. While not specifically illustrated herein, the elongated recessed slot 143 may be shaped and arranged to receive a travel stop element which, in turn, is supported by the housing 130 and likewise extends through an aperture formed transversely through the side of the guide bushing 132. This arrangement may serve to limit how far the depth extension member 134 may be axially extended or retracted relative to the guide bushing 132 and housing 130, and may also prevent the depth extension member 134 from rotating about the axis AX. However, it will be appreciated that the measurement module 128 could be configured to limit or prevent movement of the depth extension member 134 in other ways without departing from the scope of the present disclosure. The depth extension member 134 further comprises rack teeth 144. The depth extension member 134 may comprise a polymeric material. The depth extension member 134 may comprise a plastic material. It is contemplated that the depth extension member 134 may comprise a different polymeric material than a plastic material. It is also contemplated that the depth extension member 134 may comprise metal or another material different from a polymeric material. The depth extension member 134 may be formed by injection molding.

As shown in FIG. 4, the measurement module 128 includes a transducer assembly 136. The transducer assembly 136 includes a gear 146 having gear teeth 145. The gear teeth 145 are disposed in meshed engagement with the rack teeth 144 of the depth extension member 134. The gear 146 may comprise a spur gear. In some configurations, the transducer assembly 136 may be considered a displacement sensor. As shown in FIG. 5, the window 142 of the guide bushing 132 is arranged adjacent to the transducer assembly 136 to facilitate the meshed engagement between the rack teeth 144 and the gear teeth 145. Said differently, the gear 146 may extend through the window 142 of the guide bushing 132 to engage the depth extension member 134. The gear 146 may include a shaft portion 147 extending along a common gear axis CAX. The gear 146 itself is rotatable 360 degrees about the common gear axis CAX as the depth extension member 134 moves along the axis AX relative to the housing 130. A biasing member (not shown) such as a torsion spring may be mounted to the gear 146 to bias the gear 146 such that the gear 146 acts on the depth extension member 134 to bias the depth extension member 134 in a distal direction. The gear 146 may comprise a polymeric material. The gear 146 may comprise a plastic material. It is contemplated that the gear 146 may comprise a different polymeric material than a plastic material. It is also contemplated that the gear 146 may comprise metal or another material different from a polymeric material. The gear 146 may be formed by injection molding.

The transducer assembly 136 is responsive to rotation of the gear 146 resulting from axial movement of the depth extension member 134 via meshed engagement in order to generate electrical signals (i.e., a transducer signal or a displacement signal) representing changes in the position of the depth extension member 134 relative to the housing 130 along the axis AX. The position of the depth extension member 134 relative to the housing 130 corresponds to the relative positioning of the distal end of the depth extension member 134 relative to the housing 130 when the surgical drill 61 is placed against the workpiece. In some configurations, the transducer assembly 136 includes a potentiometer coupled to the gear 146 to generate the transducer signal. Thus, it will be appreciated that the transducer assembly 136 is able to provide the surgical handpiece assembly 62 with enhanced functionality. By way of example, in some configurations, the transducer assembly 136 may be disposed in communication with the controller 78, which may be configured to interrupt or adjust how the motor 84 is driven based on movement of the depth extension member 134, such as to slow rotation of the drill bit 66 at a specific drilling depth into the workpiece. The transducer assembly 136 may also be disposed in communication with an output device 148, such as a display screen, one or more light-emitting diodes (LEDs), and the like, to provide the surgeon with information relating to movement of the depth extension member 134, such as to display a real-time drilling depth, a recorded historical maximum drilling depth, and the like. Other configurations are contemplated. The output device 148 may be part of the measurement module 128 that is removable. Further, while the transducer assembly 136 and the depth extension member 134 illustrated in FIG. 4 collectively comprise a rack and pinion design with the rack teeth 144 of the depth extension member 134 and the gear 146 of the transducer assembly 136, it is contemplated that the transducer assembly 136 may comprise one or more sensors such as a potentiometer, an optical sensor, and a linear variable displacement transformer to generate transducer signals responsive to displacement of the depth extension member 134 relative to the housing 130. In some configurations, the gear 146 is not used to determine the position of the depth extension member 134, but is used to bias the depth extension member 134 distally (e.g., using the torsion spring).

As described above, certain components of the measurement module 128, including the gear 146 and the depth extension member 134, may comprise a polymeric material. Polymeric components can often be produced at low cost and have desirable sterility resistance and strength, but they are often difficult to produce with part-to-part consistency (i.e., tight tolerances across large quantities of parts are difficult to maintain). As one polymeric component can vary in size (e.g., diameter, length, tooth spacing, and tooth geometry) relative to another polymeric component of the same part, an acceptable fit or engagement between different moving parts can be compromised after assembly.

In the configuration illustrated in FIGS. 1-5, the gear backlash of the gear teeth 145 to the rack teeth 144 (i.e., the meshing engagement or fit therebetween) has a usable range of mesh clearance or tooth overlap for the gear 146 to rotate without binding or jamming and to withstand the loads experienced during use to prevent slippage or tooth skip between the gear teeth 145 and the rack teeth 144. As described above, the gear 146 is rotatably coupled to the housing 130, the guide bushing 132 is fixed relative to the housing 130, and the guide bushing 132 constrains a position of the depth extension member 134 during operation. Thus, not only is the fit between the gear 146 and the depth extension member 134 dependent on the sizes of the gear 146 and the depth extension member 134 but also the tolerance stack-up of the fixed position of the guide bushing 132 to the housing 130 and the size (e.g., diameter) of the bore of the guide bushing 132.

With reference to FIGS. 6-9, a method of assembling the measurement module 128 is provided to promote meshing engagement between the gear teeth 145 of the gear 146 and the rack teeth 144 of the depth extension member 134. The method comprises the step of disposing the depth extension member 134 within the bore of the bushing 132 and at least a portion of the housing 130. The method further comprises the step of arranging the rack teeth 144 of the depth extension member 134 to be engaged by the gear teeth 145 of the gear 146. The method further comprises the step of urging the depth extension member 134 toward the gear 146 and the rack teeth 144 into meshed engagement with the gear teeth 145. While the depth extension member 134 is urged toward the gear 146, the bushing 132 is fixed to the housing 130, via ultrasonic welding, for example.

Figure 6:
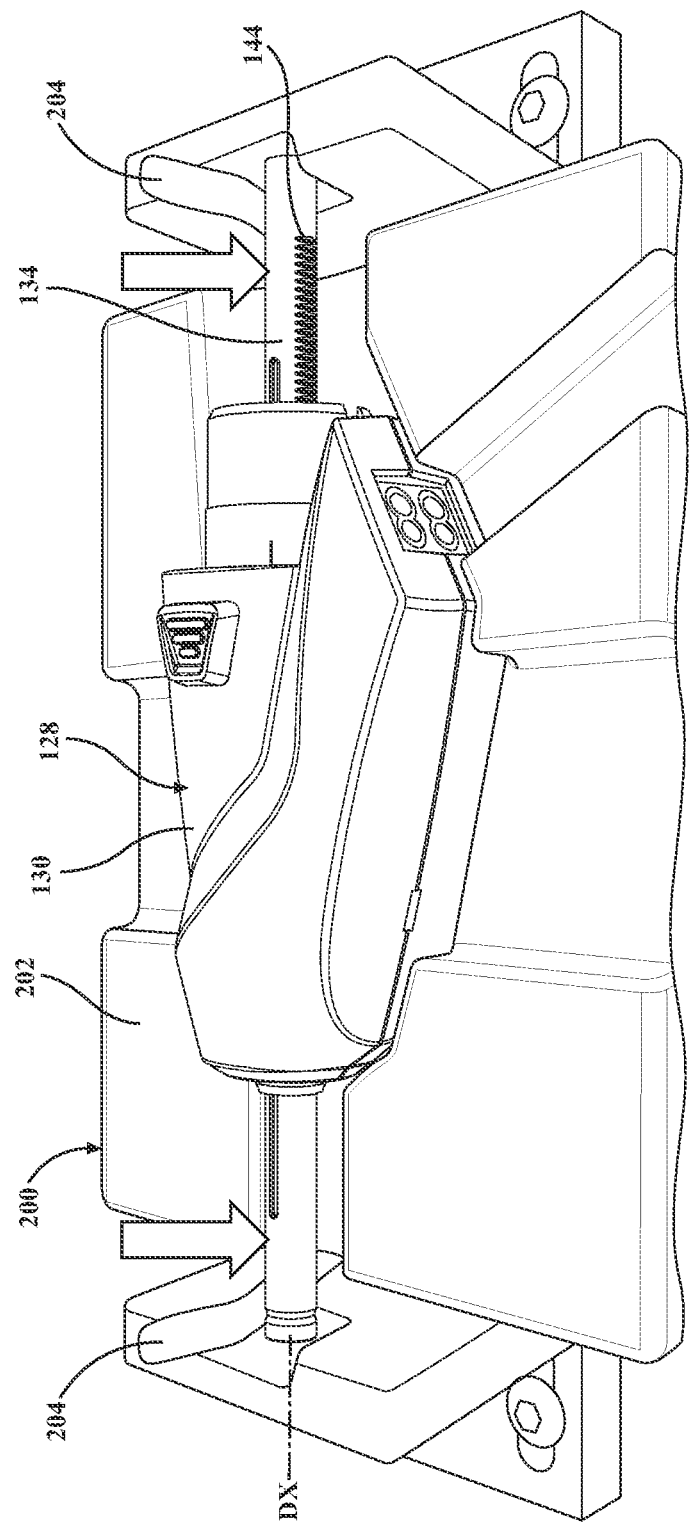
FIG. 6 is a perspective view of the measurement module in an assembly fixture.
Figure 7:
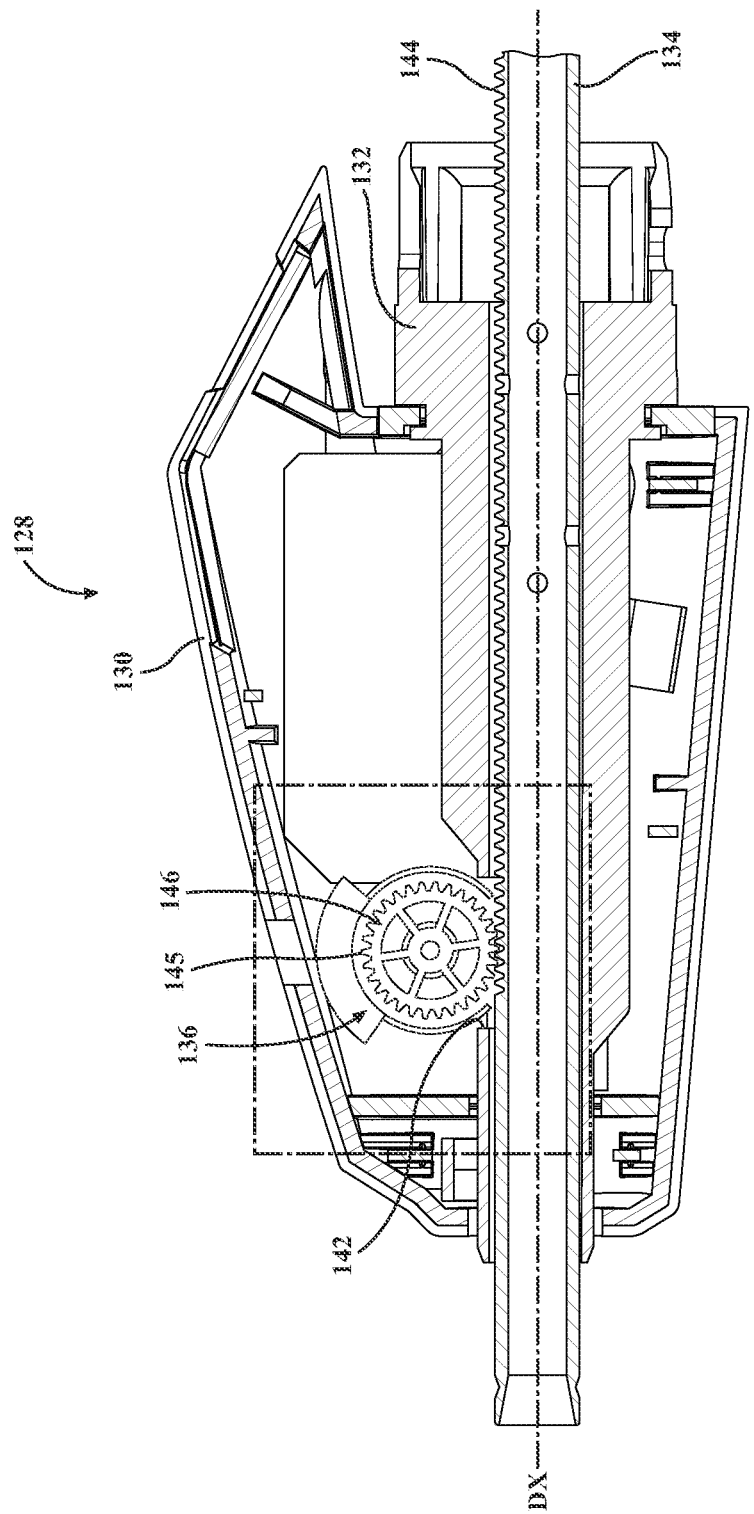
FIG. 7 is a sectional view of the measurement module.
Figure 8:
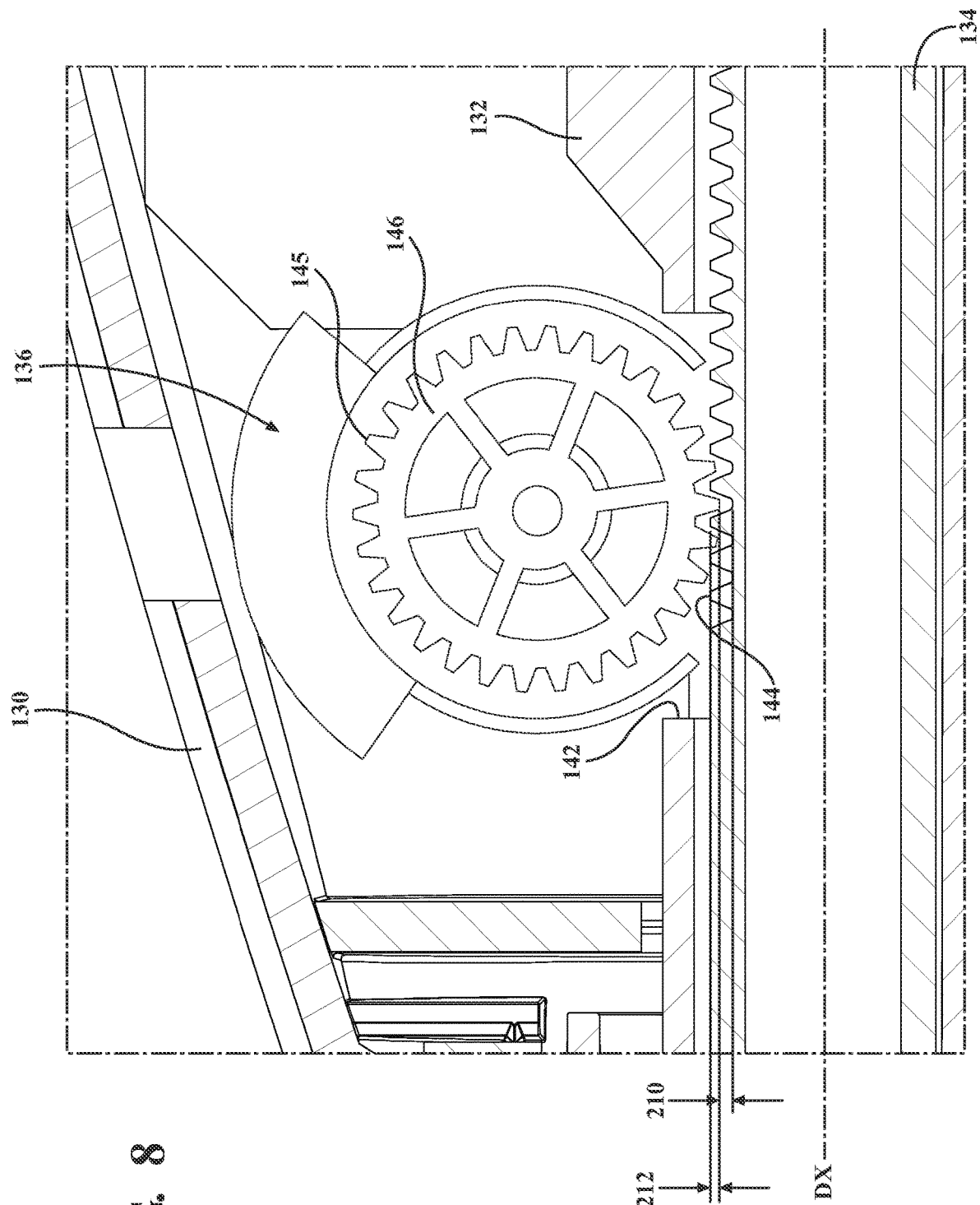
FIG. 8 is a detailed view of a portion of the measurement module shown in FIG. 7 illustrating gear teeth of a gear of the measurement module having a mesh clearance relative to rack teeth of the depth extension member of the measurement module.
Figure 9:
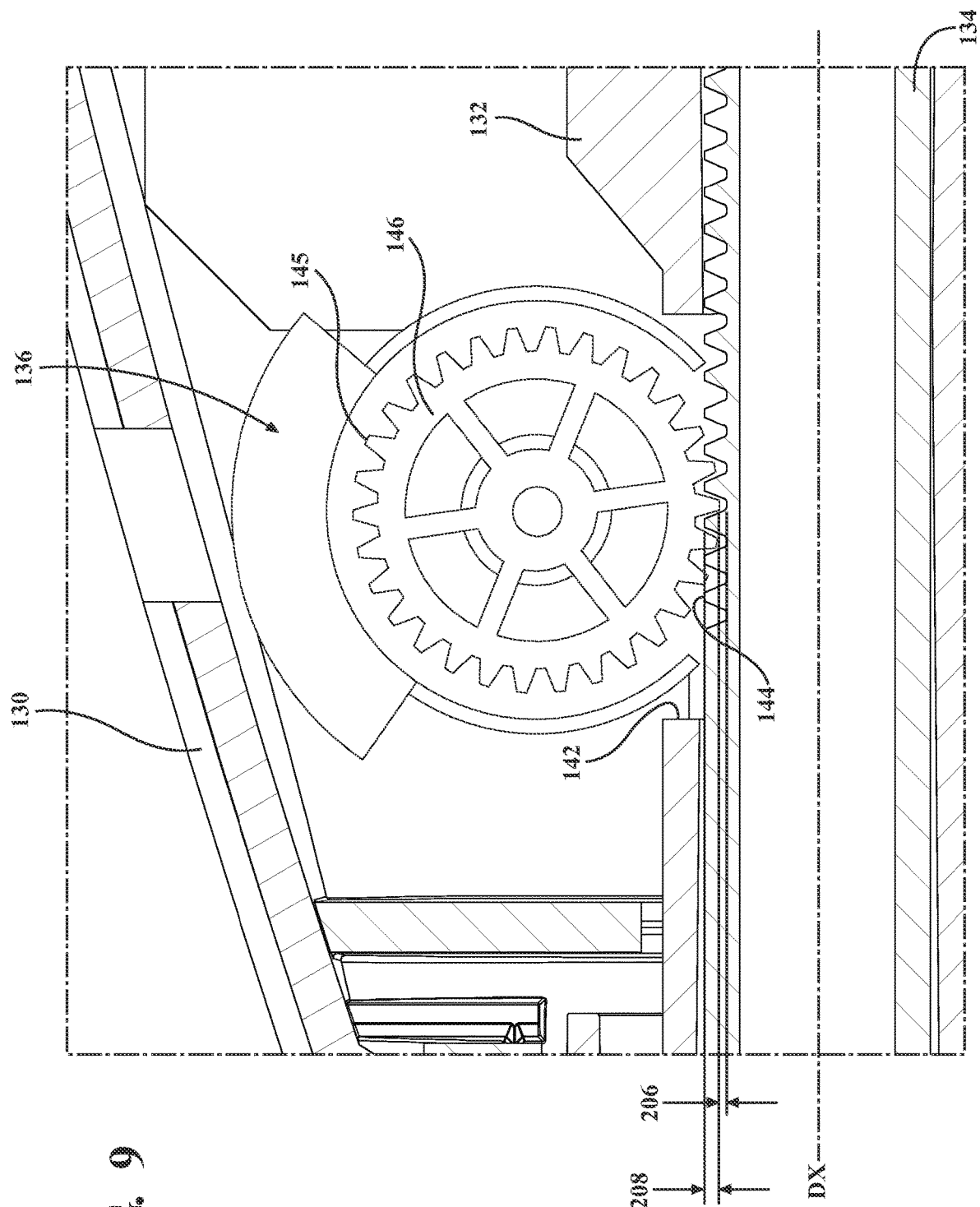
FIG. 9 is a detailed view of a portion of the measurement module shown in FIG. 7 illustrating gear teeth of the gear of the measurement module having another mesh clearance relative to rack teeth of the depth extension member of the measurement module.

In an exemplary configuration shown in FIG. 6, at least a portion of the measurement module 128 may be placed in an assembly fixture 200 to assist in urging the gear 146 and the depth extension member 134 together. The assembly fixture 200 may comprise a fixture body 202 configured to support the measurement module 128 during the ultrasonic welding operation. In the configuration illustrated in FIG. 6, the housing 130 may be placed in or on the fixture body 202 so that the position of the housing is 130 is constrained or restrained. The depth extension member 134 is disposed in the bore of the bushing 132 and both the depth extension member 134 and the bushing 132 are loosely (i.e., not yet fixed/welded or coupled to the housing 130) disposed at least partially in the housing 130.

The assembly fixture 200 may also comprise one or more biasing members 204 to urge the depth extension member 134 toward the gear 146. In the configuration illustrated in FIG. 6, the biasing members 204 are realized as spring fingers. The spring fingers may comprise metal. It is contemplated that the one or more biasing members 204 may comprise a spring, a plunger, or another deflectable component that acts to urge the depth extension member 134 toward the gear 146. Before urging the depth extension member 134 toward the gear 146, the gear 146 may be rotatably coupled to the housing 130. While the one or more biasing members 204 urge the depth extension member 134 toward the gear 146, and with the housing 130 constrained by the fixture body 202, the bushing 132 may be fixed (e.g., via ultrasonic welding) to the housing 130 so that the bushing 132 and the housing 130 are permanently joined. The depth extension member 134 may be urged toward the gear 146 while the gear 146 is received by the window 142 of the bushing 132 to facilitate the meshed engagement between the gear teeth 145 and the rack teeth 144.

In some configurations where the housing 130 comprises two or more housing components 138, the housing components 138 may be fixed (e.g., welded) together and to the bushing 132 while the measurement module 128 is in the assembly fixture 200. It is also contemplated that the housing components 138 may be separately fixed to the bushing 132 while in the assembly fixture 200. In some configurations where the housing 130 and the bushing 132 comprises polymeric materials, portions of the bushing 132 that are configured to interface with the housing 130 before being ultrasonically welded may comprise textured welding surfaces to promote plastic melt and improve weld strength between the bushing 132 and the housing 130. Alternatively, the housing 130 may comprise the textured welding surfaces. In some configurations, the housing 130 comprises two housing components 138 that are configured to collectively surround the bushing 132 as a clam shell arrangement.

While the biasing members 204 urge the depth extension member 134 toward the gear 146, the gear teeth 145 and the rack teeth 144 have a first mesh clearance 206 (see FIG. 9) relative to each other. Mesh clearance may be defined as the distance between the outermost portion of a tooth and the root diameter (i.e., innermost portion of the space between the teeth) of the mating teeth. In many cases the first mesh clearance 206 comprises a minimal clearance. In other words, the teeth 145, 144 overlap to such an extent that the gear teeth 145 and the rack teeth 144 contact each other and cannot be disposed closer to each other without deforming one or more of the gear teeth 145 or the rack teeth 144. With minimal clearance, the gear teeth 145 and the rack teeth 144 may have maximum overlap 208. While the assembly fixture 200 illustrated in FIG. 6 includes two biasing members 204, it is contemplated that a single biasing member 204 may be used. While the fixture body 202 of the assembly fixture 200 illustrated in FIG. 6 constrains the position of the housing 130 and the biasing members 204 urge the depth extension member 134 toward the gear 146, it is contemplated that the assembly fixture 200 could be reconfigured so that the fixture body 202 constrains a position of the depth extension member 134 and the biasing members 204 urge the housing 130, and thus the gear 146, toward the depth extension member 134.

After the bushing 132 is fixed to the housing 130 and the biasing members 204 cease urging the depth extension member 134 toward the gear 146 (e.g., by removing the measurement module 128 from the assembly fixture 200), the depth extension member 134 is permitted to move within the bore of the bushing 132 away from the gear 146. The inner diameter of the bore of the bushing 132 may be sized so that the bore of the bushing 132 prevents movement of the depth extension member 134 out of engagement with the gear 146, by virtue of the inner diameter of the bushing 132 approximating the outer diameter of the depth extension member 134. In this manner, the bore of the bushing 132 establishes a second mesh clearance 210 (see FIG. 8) between the gear teeth 145 and the rack teeth 144 that is greater than the first mesh clearance 206 (see FIG. 9) where the depth extension member 134 may be able to "float" or otherwise move within the bore of the bushing 132 while remaining in meshed engagement with the gear 146. The second mesh clearance 210 may be a maximum clearance in which the gear teeth 145 and rack teeth 144 are still operable in meshing engagement. With maximum clearance, the gear teeth 145 and the rack teeth 144 may have minimum overlap 212 without tooth skipping.

In many configurations, the depth extension member 134 is longer than the bushing 132 and may extend through the bore on either side of the bushing 132. The depth extension member 134 may be urged toward the gear 146 at a first point along the depth extension axis DX on one side of the bushing 132 and a second point spaced from the first point along the depth extension axis DX on the other side of the bushing 132. Said differently, the bushing 132 may be disposed between the first and second points. In some configurations, the first and second points of the depth extension member 134 are equally spaced from the bushing 132 while the depth extension member 134 is urged toward the gear 146.

The above-described method of assembly is particularly advantageous for assembly of polymeric components such as the gear 146 and the depth extension member 134 because the relative size and fit of the gear teeth 145 and the rack teeth 144 may not be subject to tolerance stack up during assembly. Moreover, a gear 146 and a depth extension member 134 of one measurement module 128 may have the same overlap, gear backlash, or mesh clearance as a measurement module 128 having different sized gear 146 or depth extension member 134. While the method is particularly advantageous for assembly of polymeric components, the method of assembly may also be advantageous for components comprising other materials. The above method of assembly mitigates the overall number of tolerance bands that contribute to the tolerance stack-up by fixing the bushing 132 to the housing 130 after the minimum mesh clearance is established between the gear teeth 145 and the rack teeth 144. Fixing the bushing 132 to the housing 130 after the minimum mesh clearance is established may provide a robust method of assembly to result in consistent, ideal tooth meshing between the gear teeth 145 and rack teeth 146 across different measurement modules 128 having identical or similar specifications.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

What is claimed is:

1. A method of assembling a measurement module used for bore depth determinations in tissue, the measurement module having a housing, a gear having a plurality of gear teeth disposed within and rotatably coupled to the housing, a bushing, and a depth extension member having a plurality of rack teeth extending along a depth extension axis, the method comprising:
   disposing the depth extension member within a bore of the bushing and at least a portion of the housing;
   arranging the rack teeth of the depth extension member to be engaged by the gear teeth of the gear;
   urging the depth extension member toward the gear and the rack teeth into meshed engagement with the gear teeth; and
   fixing the bushing to the housing while the depth extension member is urged toward the gear.

2. The method of claim 1, wherein the step of disposing the depth extension member within the bore further comprises disposing the depth extension member within the bore sized to prevent movement of the rack teeth of the depth extension member out of meshed engagement with the gear teeth of the gear after the bushing is fixed to the housing and urging of the depth extension member toward the gear ends.

3. The method of claim 1, wherein the gear teeth and the rack teeth have a first mesh clearance while the depth extension member is urged toward the gear, and wherein the gear teeth and the rack teeth have a second mesh clearance greater than the first mesh clearance after urging ends.

4. The method of claim 3, wherein the first mesh clearance comprises a minimum mesh clearance.

5. The method of claim 1, wherein the gear teeth and the rack teeth overlap a first distance while the depth extension member is urged toward the gear, and wherein the gear teeth and the rack teeth overlap a second distance less than the first distance after urging ends.

6. The method of claim 5, wherein the first distance comprises a maximum overlap.

7. The method of claim 1, wherein the bushing defines a window, and wherein the step of urging the depth extension member toward the gear occurs while the gear is received by the window of the bushing.

8. The method of claim 1, wherein the depth extension member is longer than the bore of the bushing, and wherein the step of urging the depth extension member toward the gear further comprises urging the depth extension member at a first point of the depth extension member outside of the bushing and urging the depth extension member at a second point of the depth extension member outside of the bushing spaced from the first point along a length of the depth extension member with the bushing disposed between the first and second points.

9. The method of claim 8, wherein the first and second points of the depth extension member are equally spaced from the bushing while the depth extension member is urged toward the gear.

10. The method of claim 1, further comprising a potentiometer to generate a displacement signal responsive to rotation of the gear.

11. The method of claim 1, further comprising restraining one of the housing and the depth extension member in a fixture, and wherein the step of urging the depth extension member toward the gear further comprises urging one of the depth extension member and the housing toward the other of the depth extension member and the housing such that the depth extension member and the gear are disposed in meshing relationship with minimal meshing clearance.

12. The method of claim 1, further comprising the step of forming the depth extension member from a polymeric material.

13. The method of claim 12, wherein the step of forming the depth extension member further comprises forming the depth extension member from injection molding.

14. The method of claim 1, further comprising the step of forming the gear from a polymeric material.

15. The method of claim 14, wherein the method of forming the gear further comprises forming the gear from injection molding.

16. The method of claim 1, wherein the step of fixing the bushing to the housing comprises ultra-sonic welding the bushing to the housing.

\* \* \* \* \*